US006788409B2

(12) United States Patent
Goodwin

(10) Patent No.: US 6,788,409 B2
(45) Date of Patent: Sep. 7, 2004

(54) FLOW CELL SYSTEM FOR SOLUBILITY TESTING

(75) Inventor: Joseph J. Goodwin, Littleton, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/233,645

(22) Filed: Sep. 3, 2002

(65) Prior Publication Data

US 2003/0067594 A1 Apr. 10, 2003

Related U.S. Application Data

(60) Provisional application No. 60/317,849, filed on Sep. 7, 2001.

(51) Int. Cl.[7] .............................................. G01N 21/00
(52) U.S. Cl. ....................... 356/339; 356/441; 356/73
(58) Field of Search .......................... 356/73, 246, 437, 356/336, 337, 338, 339

(56) References Cited

U.S. PATENT DOCUMENTS

| | | | |
|---|---|---|---|
| 3,699,336 A | 10/1972 | Ehrlich et al. | 356/39 |
| 3,801,280 A | 4/1974 | Shah et al. | 436/2 |
| 4,660,971 A | 4/1987 | Sage et al. | 356/73 |
| 4,750,837 A | 6/1988 | Gifford et al. | 356/246 |
| 4,774,055 A | 9/1988 | Wakatake et al. | 422/64 |
| 5,093,234 A | 3/1992 | Schwartz | 356/213 |
| 5,331,958 A | 7/1994 | Oppenheimer | 356/39 |
| 5,339,255 A | 8/1994 | Suzuki et al. | 356/51 |
| 5,736,410 A | 4/1998 | Zarling et al. | 356/244 |
| 6,400,453 B1 | 6/2002 | Hansen | 356/237.1 |
| 6,537,829 B1 | 3/2003 | Zarling et al. | 356/246 |
| 6,553,849 B1 | 4/2003 | Scofield et al. | 356/336 |
| 2002/0195554 A1 | 12/2002 | Staton et al. | 250/252.1 |

OTHER PUBLICATIONS

J. Goodwin et al., A New Rapid Technique for Sensitive Solubility Measurements: A Flow Cytometric Approach, Nov., 1999, presented at AAPS—New Orleans, LA 1999.

J. Goodwin et al., A New Rapid Technique for Sensitive Solubility Measurements: A Flow Cytometric Approach, Sep., 1999, presented at Society for Biomolecular Screening—.

(List continued on next page.)

*Primary Examiner*—Michael P. Staftra
*Assistant Examiner*—Juan D Valentin II
(74) *Attorney, Agent, or Firm*—Stevens, Davis, Miller & Mosher, LLP

(57) ABSTRACT

The invention provides a flow cell system for high throughput solubility testing of compounds that is particularly useful for screening large compound collections, such as combinatorial chemical libraries or other such synthetic chemical libraries. The system includes a flow cell to channel a fluid sheath which itself channels a continuous or intermittent sample liquid stream containing a compound for testing. Where the concentration of compound in the sample exceeds the solubility limit, particles of the test compound precipitate. These particles scatter the light from an interrogating light beam directed at the sample liquid stream. Individual flashes of scattered light are detected as electronic pulse signals from the detector and their intensity analyzed according to intensity and number of events. System software analyzes the stored pulse signal data in real-time to determine whether there is a significant increase in scattering over the highly variable background scattering. The software then outputs a signal to effectuate selection of a subsequent sample, which may be a higher concentration sample of the same compound or a sample of a subsequent compound for solubility testing. The system also automatically realigns the sample liquid flow after a preset number of samples or in the event that control particles or beads are not efficiently detected.

31 Claims, 4 Drawing Sheets

OTHER PUBLICATIONS

Operating Instructions for FACSCount—HS Prototype, Becton Dickinson Biosciences Discovery Labware (Apr. 24, 2002).

Bevan, et al., A High–Throughput Screening Method for the Determination of Aqueous Drug Solubility Using Laser Nephelometry in Microtiter Plates, Analytical Chemistry, vol. 72, No. 8, Apr. 15, 2000, pp. 1781–1787.

Hill, et al., Rapid Screening of Aqueous Solubility by a Nephelometric Assay.

Lipinski, et al., Experimental and Computational Approaches to Estimate Solubility and Permeability in Drug Discovery and Development Seetings, Advanced Drug Delivery Reviews, 23 (1997) 3–25.

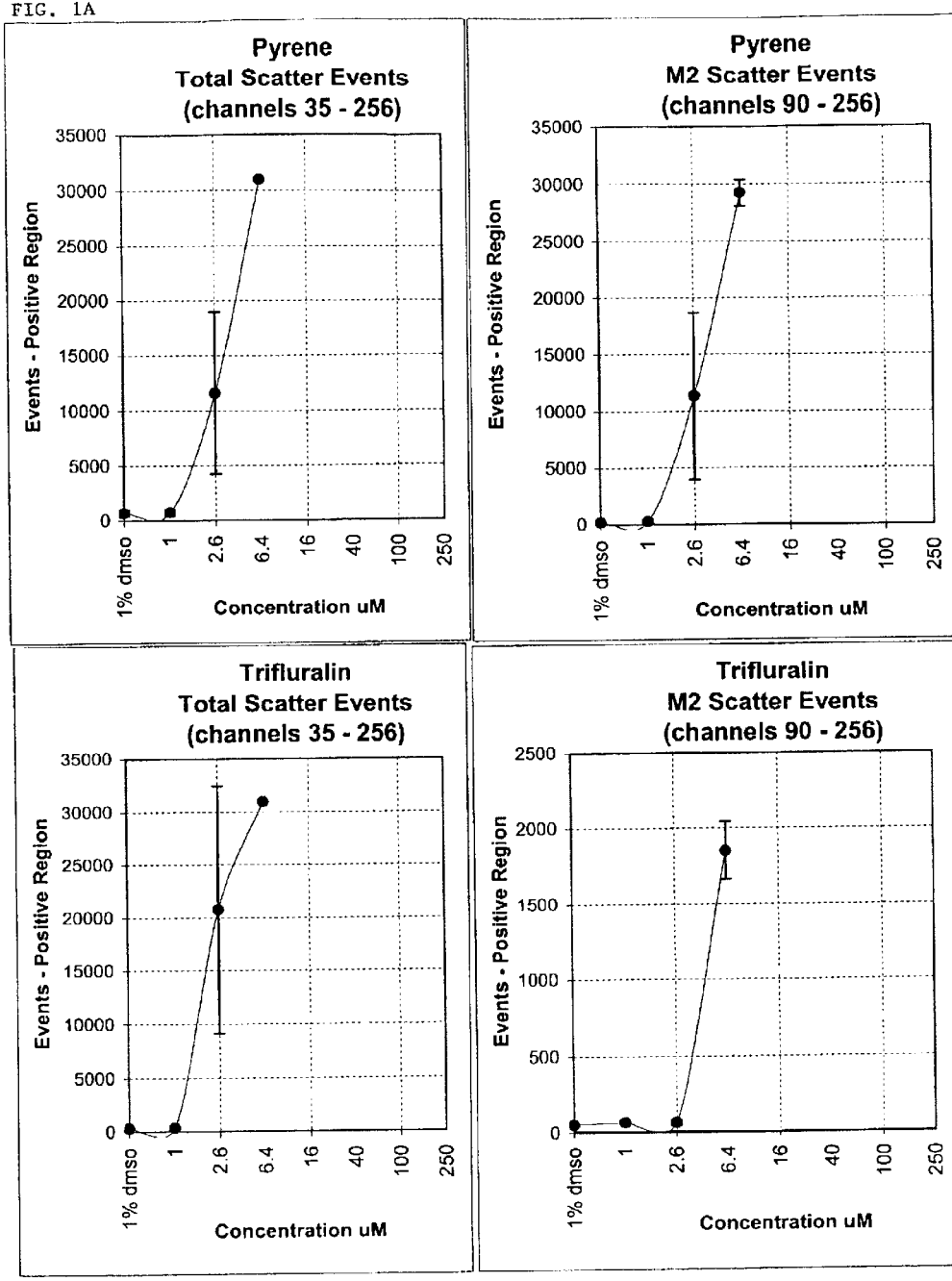

FLOW CELL SYSTEM FOR SOLUBILITY TESTING

This application claims the benefit of U.S. Provisional Application Serial No. 60/317,849, filed on Sep. 7, 2001.

BACKGROUND OF THE INVENTION

1. Field of the Invention

This invention relates to the field of high throughput solubility testing of compounds in flow cell devices. The invention relates in particular to the automated analysis of data collection and sample selection, as well as to automated procedures for realignment of sample flow.

2. Background

Solubility testing of new chemical entities (NCEs) is an important step in assessing their potential utility as pharmaceutical agents. Many compounds are rejected as having too low an aqueous solubility for adequate bioavailability to be useful in drug development.

Turbidity measurement has become popular as an indicator of the aqueous solubility of potential lead compounds. In drug development, turbidity is most commonly evaluated using microtiter plate-based nephelometers that measure the light scattering by the sample, or alternatively, standard laboratory turbidimeters which measure the change in transmitted light. In either case, compound precipitate is detected by passing light from a light source through some portion of the sample and evaluating light scattering.

With nephelometry plate readers, the sample is stationary (in the microtiter well), light is directed through the plate and off-axis forward-scattered light is used to detect the precipitate. By contrast, with turbidimeters, usually a portion of a stirred sample (often several milliliters) is passed through the turbidimeter and the reduction in transmitted light due to scattering is measured to obtain a turbidity reading.

At low concentrations of particulates, the change in transmitted light, viewed from straight on, is so slight that the reduction is virtually undetectable by any means. At higher concentrations the attenuation in transmitted light becomes easier to detect due to multiple scattering which interferes with direct transmission.

A solution to the problems described above is to measure the light scattered at an angle to the incident light beam and then relate this off-axis scattered light to the turbidity of the sample. Most instruments of this type measure the 90 degree scatter because light scattered at this angle is considered to correlate more precisely with particle concentration. These types of instruments are referred to as nephelometers.

Both of these technologies work by detecting multiple compound particles suspended within a given sample volume. The number of particles suspended in the liquid, the size of each particle and the light scattering properties of the particles are all critical factors that affect the sensitivity of a turbidimeter or a nephelometer. In addition, the intensity and focus of the light source and the sensitivity of the light detection mechanism are also important instrument properties that affect accuracy and sensitivity depending on the method used.

Nephelometry has been used extensively in the art to determine solubility limits of test compounds. See for example Dressman et al., *Pharmaceutical Research*, 15(1): 11–22 (1998). This technique has been adapted to high throughput screening by the capacity to read directly from microtiter plates. See for example Bevan and Lloyd, *Analytical Chemistry* 72: 1781–1787 (2000).

Light scattering has also been used for solubility testing of compounds for drug development (Lipinski et al. *Advanced Drug Delivery Reviews* 23: 3–25 (1997). These authors followed the absorbance increase due to light scattering by precipitated particulate material with a dedicated diode array UV machine.

Recently, the field has turned to high throughput flow cytometer systems adapted to light scattering to follow the precipitated particulates in a sample. See for instance Goodwin et al., A New Rapid Technique for Sensitive Solubility Measurements: A Flow Cytometric Approach. Published presentations from meetings of The Society for Biomolecular Screening, Edinburgh, Scotland, September 1999; and AAPS, New Orleans, La., November 1999.

Despite the successful application of flow cytometry to solubility testing, some problems still remain. Many problems associated with turbidimeters and nephelometers also plague the flow cell systems currently in use. For instance, non-uniformity of samples, due to impurities, solvent absorption, and precipitation of contaminants cause spurious light scattering. Also, anomalous scattering may be due to solvent scatter, dissolved impurities and such contaminants as solvent extractables from labware, e.g. microtiter plates etc.

There is still a need for an improved, accurate, robust flow cells system that is adaptable to high throughput screening of large numbers of compounds, that discriminates precipitated compound particles on the basis of size distribution from random background interference due to impurities from solvents, solvent extractables and other impurities and contamination. Further, the system should be capable of automatic detection and correction of misalignment of the sample liquid stream.

SUMMARY OF THE INVENTION

The present invention provides a flow cell system for solubility testing of a compound in a sample liquid; the system including the following components:

(a) a flow cell suitable for channeling a fluid sheath flowing through the flow cell, the fluid sheath directing a continuous or intermittent sample liquid stream, wherein the sample liquid stream comprises particles of the compound for solubility testing;

(b) a light source for illuminating the sample liquid stream in the flow cell and producing scattered light flashes from the particles of the compound;

(c) a detector for detecting the scattered light flashes and generating an electronic pulse detection signal for each light flash to provide raw sample data, each light flash having a light intensity and each electronic pulse detection signal having a pulse amplitude corresponding to the intensity of the detected light flash; and (d) a means for real-time processing of multiple electronic pulse detection signals, wherein each of the signals is allocated to one of a series of channels, each channel detecting electronic pulse detection signals within a preset signal amplitude range, to provide multichannel sample data, and outputting the sample data for effectuating selection of a subsequent sample liquid from a plurality of subsequent sample liquids for solubility testing.

The flow cell according to the present invention may further include a means for storage and recall of the raw sample data and/or the multichannel sample data. Samples for solubility testing may be provided in the wells of a microtiter plate, which may include several dilutions of the sample for solubility testing.

The flow cell system of the present invention may also include a reservoir for containing a control substance for assessing the alignment of the sample liquid flow in the flow cell. The control substance may be a particle or a bead.

The invention also provides a method for solubility testing of a compound in a sample liquid; the method including the following steps:

(a) providing a flow cell suitable for channeling a fluid sheath flow through the flow cell, the fluid sheath flow directing a continuous or intermittent sample liquid stream, wherein the sample liquid stream comprises particles of the compound for solubility testing;

(b) illuminating the sample liquid stream in the flow cell to provide scattered light flashes from the particles of the compound;

(c) detecting the scattered light flashes to provide raw sample data and generating an electronic pulse detection signal for each light flash, each light flash having a light intensity and each electronic pulse detection signal having a pulse amplitude corresponding to the intensity of the detected light flash;

(d) processing of multiple electronic pulse detection signals in real-time, wherein each of the signals is allocated to one of a series of channels, each channel detecting electronic pulse detection signals within a preset signal amplitude range; and (e) outputting the sample data to a means for effectuating a selection of a subsequent sample liquid from a plurality of subsequent sample liquids for solubility testing.

Multiple sample liquids for solubility testing may be provided in the wells of a microtiter plate. After solubility testing of the first sample liquid, subsequent sample liquids may include a series of higher dilutions of the same compound for solubility testing and may also optionally include a series of dilutions of one or more additional compounds for solubility testing.

The method of the present invention may be applied to a flow cell system that includes a reservoir for containing a control substance for assessing the alignment of the sample liquid flow in the flow cell. Alternatively, the control substance may be provided in one or more wells of a microtitier plate. The control substance employed may be a particle or a bead.

In another aspect the above methods further include the following steps for selection of the subsequent sample liquid: Either selecting one of the series of higher concentrations of the compound in the event that the multichannel sample data indicates the absence or low levels of particles of the compound; or selecting one of the series of increasing concentrations of the second compound for solubility testing in the event that the multichannel sample data indicates the presence of significant levels of particles of the compound.

The present invention also provides a means for real-time processing of multiple electronic pulse detection signals from a flow cytometer adapted for solubility testing, wherein each of the signals is allocated to one of a series of channels, each channel detecting electronic pulse detection signals within a preset signal amplitude range, to provide multichannel sample data, and outputting the sample data for effectuating selection of a subsequent sample liquid from a plurality of subsequent sample liquids for solubility testing.

The present invention further provides a means for real-time processing of multiple electronic pulse detection signals from a flow cytometer adapted for solubility testing, wherein each of the signals is allocated to one of a series of channels, each channel detecting electronic pulse detection signals within a preset signal amplitude range to provide multichannel control substance data, and thereby determining whether the sample liquid stream is aligned or misaligned, and outputting an effectuator signal if the sample liquid stream is misaligned, and initiating a corrective realignment process upon receiving the effectuator signal.

BRIEF DESCRIPTION OF THE FIGURES

FIGS. 1A–1C shows the light scattering data collected from solubility determinations of pyrene (F12), trifluralin (F13) and danazol (F18) in the Example.

DETAILED DESCRIPTION OF THE INVENTION

Figure 2:
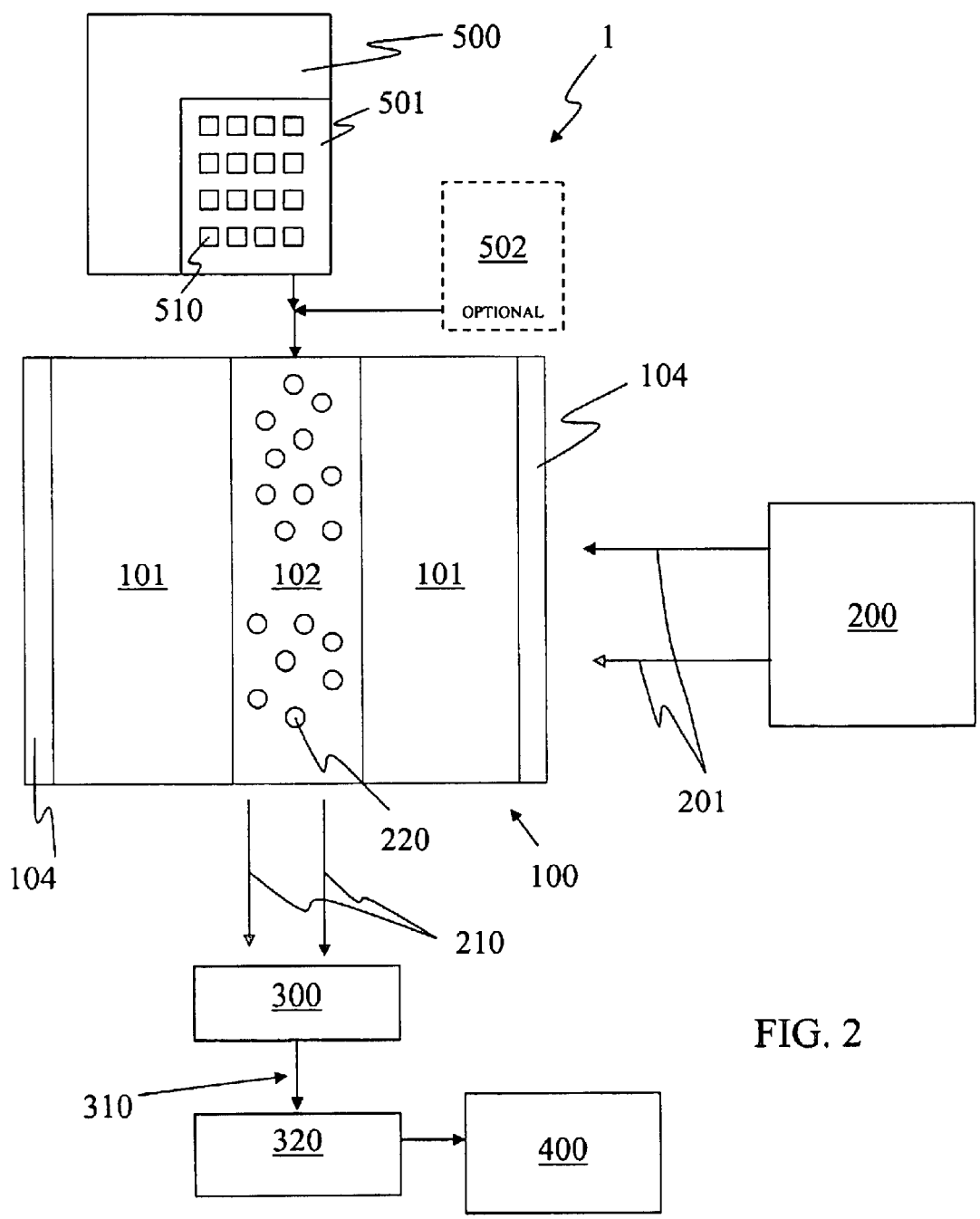
FIG. 2 shows a diagram of a typical flow cell system according to the present invention.
Figure 3:
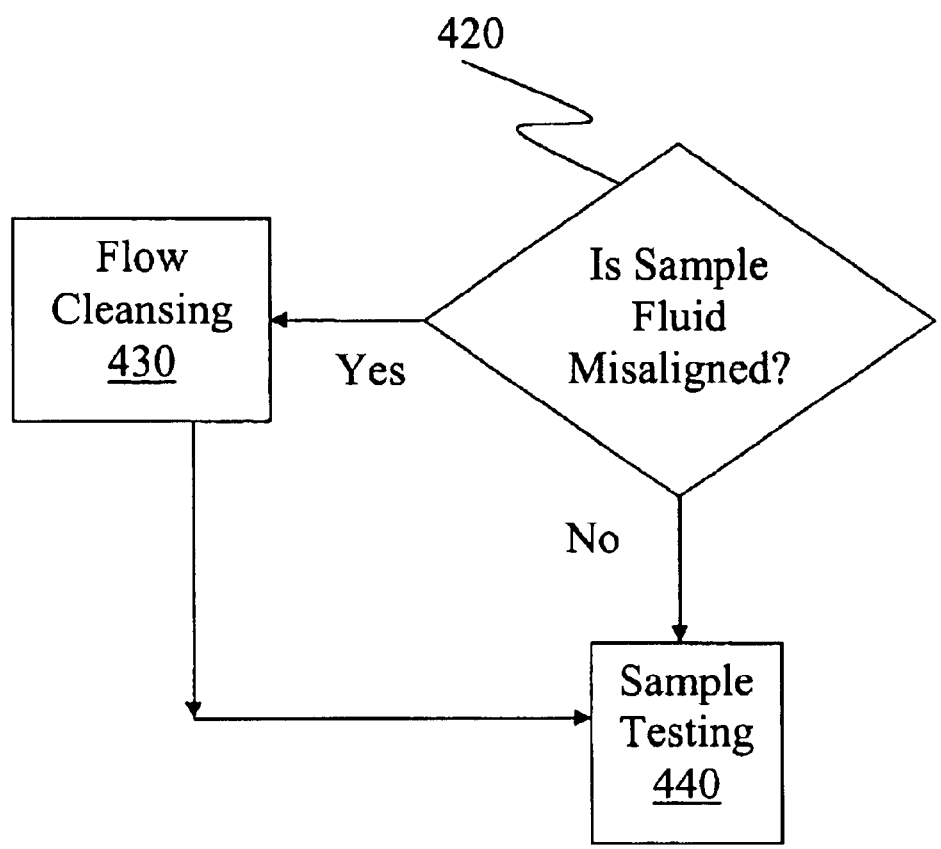
FIG. 3 shows a schematic of these sample and alignment system routines.

A diagram of a typical flow cell system 1 according to the present invention is depicted in FIG. 2. The system includes a flow cell 100, a sample selection device 500, a light source 200, one or more detectors 300 to detect scattered light and provide an electronic pulse signal corresponding to each flash of scattered light detected. Further the system includes a computer or microprocessor device 400 to receive the electronic pulse signals from the detector or detectors, and assign each signal to a predetermined channel based on the electronic signal amplitude, corresponding to the intensity of the light flash. The computer or microprocessor device 400 also processes the signal data into preset multiple channel ranges and compares the data from each of the multiple channel ranges. The computer or microprocessor device 400 thereby determines whether the next sample selected should be a further dilution of the same compound or whether to begin a series of dilutions of a subsequent sample compound. In the event that the system detects that the sample fluid stream is misaligned (step 420 of FIG. 3), the computer or microprocessor device 400 interrupts the series of sample tests and initiates a flow cell cleansing routine (step 430 of FIG. 3) before resuming sample testing (step 440 of FIG. 3). A schematic of these sample and alignment system routines is described and illustrated in conjunction with FIG. 3.

Analysis of precipitates formed in solutions of test compounds by flow cytometry has the advantage that this system involves the detection, collection and analysis of data from individual precipitation events. Hydrodynamic focusing of the sample in the flow-cell 100 narrows the sample stream such that individual particles can be characterized. This approach is not only significantly more sensitive than turbidimetry or nephelometry techniques, but also increases the accuracy and robustness of the solubility determination and can be adapted to real time processing of large numbers of samples for high throughput solubility screening.

As used herein, the term "sample liquid" 102 refers to the liquid to be tested in the flow cell 100 for the presence of particles 220 by interrogation with a light beam 201. The sample liquid 102 may be any liquid that is to be submitted for solubility testing of a test compound dissolved therein. Preferably, the sample liquid 102 is an aqueous sample liquid. The sample liquid 102 may contain between about 0.01% and about 5% of a non-aqueous solvent. Preferably the sample liquid 102 contains between about 0.02% and about 2% of non-aqueous solvent. Optimally the sample liquid 102 contains about 1% of the non-aqueous solvent. Preferred non-aqueous solvents useful for introduction of the compound for solubility testing are miscible with water.

Initially, the test compound for solubility testing may be provided as a solution in the non-aqueous water-miscible solvent. The test compound may be provided at any concentration, usually at between about 1 mM and 100 mM, with a concentration of about 10 mM being preferred. The water-miscible non-aqueous solvent may be any water-miscible non-aqueous solvent, such as for instance, dimethylsulfoxide (DMSO), methanol, ethanol, or solvents such as acetonitrile, as used in elution from HPLC (High performance liquid chromatography) systems.

The solution of the compound in the water-miscible non-aqueous solvent is diluted in a suitable aqueous buffer and mixed before samples are subjected to light scattering analysis in the flow cytometer of the invention at predetermined intervals. In preferred embodiments of the methods of the present invention solubility determinations have been found to be optimally determined at 15 minutes, 120 minutes and 24 hours after a hundred fold dilution into aqueous buffer from the solution in non-aqueous solvent, preferably 100% DMSO.

As used herein, the term "fluid sheath" refers to the liquid 101 flowing between the walls 104 of the flow cell 100 and the sample liquid 102, as shown in FIG. 2 to surround the sample fluid 102 as it flows through the flow cell 100. Suitable fluid sheath liquids include any liquid that is transparent to the interrogating light beam and compatible with the sample liquid. A preferred fluid sheath liquid is FACSflow™ (Becton Dickinson Immunocytometry Systems, San Jose, Calif.).

Useful buffers for use in the flow cell systems of the present invention may be buffered at any suitable pH. In one embodiment the buffer may be set at any pH from about pH 1 to about pH 8. In a preferred embodiment the buffer may be set at a near neutral pH, such as a pH of about 7.4.

As used herein, the term "sample liquid stream" refers to the stream of sample liquid 102 channeled through the flow cell and bounded by the fluid sheath, as is shown in FIG. 2. The sample liquid 102 stream may be a continuous flow or intermittent, forming droplets of sample liquid within the fluid sheath 101. The sample liquid 102 is preferably buffered at a particular pH, usually between about pH 1 and about pH 8. The buffering pH levels chosen may be any pH level in the range. Integral number pH buffers are convenient. Data obtained from samples at integral pH levels may be used to interpolate to intermediate pH values to give solubility profiles across a pH range.

The term "flow cell" 100 as used herein and shown in FIG. 2, refers to the receptacle through which fluid sheath 101 and sample liquid stream 102 pass during interrogation by the light beam 201 from the light source 200. The flow cell 100 is incorporated into a flow cytometer instrument, such as for instance, the BD FACScan cytometer, or the BD FACScount cytometer (Becton Dickinson Biosciences, San Jose, Calif.). The light source 200 may be any high intensity light source, such as a laser light source or a halogen source or other such light source.

Light flashes 210 scattered by the individual particles 220 within the sample liquid 102 stream are registered by a detection device 300 such as a photomultiplier tube, a light sensitive diode, a charge-coupled detector (CCD) or other such detection device.

Light is scattered in the flow cell 100 by particles 220 passing through the accurately and immovably positioned light beam 201. The particles 220 include particles of the compound being tested that have precipitated in the aqueous buffer. As these particles 220 pass through the flow cell 100 they pass through the position of the light beam 201 and cause flashes of light 210 to be scattered as the particles 220 pass the beam. The intensity of the flash of scattered light 210 is a function of the size and granularity (texture) of the particle 220. Thus, each particle 220 that passes through the light beam 201 provides a signature flash 210 with an intensity related to the size of the particle 220.

This individual particle scatter information as harvested by the flow cell system of the present invention provides selective discrimination of particle scattering from background scattering. Background scattering includes all sources of random light scattering events, including all sources of fluidic noise. Fluidic noise includes light scatter noise from the sample stream and the fluid sheath stream. The system and methods of the present invention permit the selective discrimination of particle scattering from scatter interference. Such scatter interference includes light scatter from the non-aqueous solvent and from extractables eluted by the non-aqueous solvent. For example, when sample compounds are prepared in DMSO polystyrene polypropylene microtiter plates should be avoided, as extractable impurities that contribute to the light scattering are found to leach from these plates.

Further, the system permits discrimination of other impurities such as any contaminating co-purified chemical side reaction products that may be present as well as random particulate matter by analysis of the precipitate size distribution within the sample.

In addition, the individual particle analysis provided by the system and methods of the present invention may provide information about the purity or identity of the compound undergoing solubility testing. This is possible due to the ability to collect and analyze individual particle scatter information that is capable of discriminating several distinct particle size ranges simultaneously.

These random events may be distributed differently among the different channel ranges detected by the system of the present invention and may thereby be excluded from the solubility analysis of the compound being tested by analyzing only channel ranges that are least affected by such contaminant noise, and background and solvent noise. This approach permits more accurate detection and discrimination of particle precipitation in an automated fashion in real-time.

The scattered light may be collected from any direction. Preferably, the scattered light is collected from one of two directions: forward scatter or side scatter. Most preferably, side scattered light is detected as this is the most sensitive parameter for low intensities. Ninety degree scattered light is optimal and provides the most sensitivity.

Scattered light 210 (or fluorescence from the particles 220) at 90 degrees in relation to the incident light beam 201 is collected by one or more of a series of detectors (photomultiplier tubes—PMTs) identified herein as detector or PMT 300. Any number of PMTs 300 may be used. In one embodiment the flow cell of the present invention has three PMTs, however more PMTs may be used in other flow cell systems.

In a particular instrument according to the present invention, one PMT is used for the solubility assay that collects scattered light at the wavelength of a 3 milliwatts (mW) diode laser (636 nm+/−10 nm) for high sensitivity and stability. A second PMT may used in the commercial versions of the instrument to detect light slightly above the wavelength of the laser to pick up compounds that may be excited by the laser light and emit fluorescent light.

As the light enters the PMT 300, it is converted into an electronic signal 310 and is captured and evaluated if it meets certain criteria (degree of brightness compared to a threshold). If the scattered light exceeds the preset threshold, it is processed (through logarithmic or linear amplifiers) and saved to a file (called a ECS or listmode file) 320 that contains the raw data.

The sample analysis continues for a convenient preset period of time (such as, for instance a 5 second period) or number of light flash "events" (such as, for instance 50,000 events) and all the information for that particular sample are saved into the raw data file 320. The listmode file 320 contains all the raw data from a given sample including all the information that was gathered in each detector (PMT or diode detector) for each individual event.

Alternatively, the system may be designed such that the sample collection and analysis software may be preset to count either a fixed number of events, or for a preset time interval, whichever occurs first. Generally, preset times are preferred, as samples with low particle numbers would occupy the flow cell device for unnecessarily long time periods.

The light scatter events are categorized into separate intensity groupings referred to as "channel ranges" according to the intensity of each event. The settings of the channel ranges may be pre-selected according to the requirements or selections of user of the flow cell system of the invention. Alternatively, the "channel ranges" may be determined post acquisition during the analysis of the raw scatter files based on the distribution of particle and interfering scatter in the samples. This is preferably done by automated computer analysis of the scatter profiles. In an alternative embodiment, the intensity of individual particle flashes and the number of flashes in particular channels can be used to segregate particles from interfering scatter and to provide information about the amount and quality of precipitate formed. This information is then automatically stored in a raw data file for every event detected in a given sample. In particular embodiments the detector provides either 256 channels (for low resolution systems) or 1024 channels (high resolution), each sensitive to different degrees of intensity of the detected flash event arranged in order of increasing intensity.

The flow cell system of the present invention also comprises a processing means, identified in FIG. 2 as the computer or microprocessor device 400, for executing a software-encoded or hardware-encoded program for real-time processing of the signal data 310 collected in each of the multiple channel ranges. The processing means 400 thereby compares the signals in each of these multiple channel ranges with the signals obtained from buffer only control samples and determines which of the multiple channel ranges provides the most significant data for comparison with the data obtained from the buffer controls.

In some cases this would be the channel range that includes the widest range of channels, in other cases the most significant range may be a narrower range that excludes random interfering signals from contaminants. These contaminants may include impurities or solvent extracted compounds and other particles that may be present that are not derived from the compound undergoing solubility testing.

Light scattering determinations are generally performed on several concentrations of a test compound. Upon determination of a concentration dependent increase in light scattering events in a particular selected multiple channel range, the solubility limit of a particular compound may be determined and solubility testing of further concentrations of this compound is unnecessary. The real-time processing means of the invention as described above may be programmed to output a signal to effectuate selection of a dilution of a second sample compound for solubility testing, omitting any further samples of other concentrations of the initially tested compound.

Real-time processing of the signal data collected in each of the multiple channel ranges derived from a control substance such as a particle or bead preparation is also useful for assessment of the alignment of the sample liquid stream in the flow cell. Sample compound liquids for solubility testing may be regularly interspersed with determinations using a control substance. The control substance should be of a known concentration and of a uniform particle size so that each determination should provide a standard number of scattering events and generate signal intensities within a narrow band. These signals should all fall within a narrow channel range. Observation of a standard number of scatter events within the expected narrow channel range therefore confirms that the flow cell is properly aligned.

By contrast, in the event that the number of events is below the standard number or if the signals fall outside the standard narrow channel range, the flow cell is misaligned and a cleansing cycle is required to realign the sample liquid flow. Realignment is preferably initiated by a signal from the processing means in real time to effectuate a cleansing cycle. The cleansing may be any routine that realigns the sample liquid flow, such as for instance back-flushing the flow cell with sheath fluid; draining and refilling the flow cell or flushing the flow cell with a cleansing agent such as a bleach solution.

Beads useful as control substances in the present invention may be any small beads that are size compatible with the flow cell and having light scattering properties that allow sensitive and accurate detection by the detector chosen for the particular flow cell system. Particularly favored beads include the Nile Red polystyrene latex microspheres of $2.49\mu$ diameter available from Molecular Probes Inc., Eugene, Oreg.

When beads are used as the control substance and scattered light or fluorescence of a particular intensity is detected and stored as the readout, then there would be no difference between this detection mode and the sample data collection mode. However, if the sample stream alignment monitoring involves a mechanism that is independent of the light beam and system optics, then the sample and control substance detection systems would be distinct from each other. In the latter case, there would be no "channel separation" involved in the alignment monitoring process. For example, the alignment monitoring system may employ a dye injection system and interrogation by the laser beam followed monitoring the dye by light absorption. Absorption may be followed by any means, such as for instance with any adaptable photosensitive instrument, such as a camera, a CCD or the like.

A preferred method for setting and checking system alignment of the flow within the flow cell is with beads as the control substance. This method verifies not only the position of the sample stream, but also the other variables that may affect the sample quality. Such factors that may affect the sample quality include for instance, sample flow rate, laser intensity, optical variables, alignment, blockages or other contamination, and the like. These factors may affect the number of beads detected due to the precision of the bead position within the flow.

Sample compounds for testing are preferably provided in wells 510 of a microtiter plate 501 of the sample selection device 500, though any multiple sample feeder may be accommodated by the present system. The microtiter plate may comprise any number of wells 510; 96 well and 384 well plates are in common use and are preferred, but other useful plate sizes with different sample groupings are also available. The system of the present invention may be adapted to select from any size microtiter plate 501.

Light scattering events are preferably determined at more than one time interval after mixing of the sample liquid by stepwise dilution of a concentrated stock solution in non-aqueous solvent (usually DMSO). It has been found that determinations of light scattering by the diluted compound solutions for solubility analysis in the flow cell of the present invention provide optimum results at about 15 minutes, 120 minutes and 24 hours after mixing. Thirty microliter samples were found to be convenient for high throughput screening and suitable for accurate readings at high sensitivity.

In a preferred embodiment, an automated alignment bead injection routine is interspersed between test sample determinations during the analysis of samples from a microtiter plate. This allows frequent checking and confirmation of the alignment of the sample liquid flow. The sample liquid flow may be easily diverted from the path of the light beam by obstructions to the normal flow of the sheath fluid causing redirection of the sample liquid, for example due to bubbles or contaminant buildup on the walls of the flow cell. Beads may be supplied from a separate reservoir to conserve the number of wells available for samples for solubility testing.

Alternatively, at predetermined intervals (such as, for instance after completing the testing of samples of every three columns from the microtiter plate) the system may be programmed to return to a well containing beads located on the microtiter plate 501 to repeat an alignment check of the sample fluid stream. The wells 510 of column 1 of the microtiter 501 plate may be reserved for bead and buffer controls.

In another alternative embodiment, the bead and buffer controls may be obtained from separate reservoirs, one shown in FIG. 2 at 502, thus freeing more wells 510 for sample compounds. Selection and comparison of bead and buffer control samples allows verification that beads are found within a certain intensity range (e.g. within an expected, such as for example, a 10 channel range from a total of 256 channels, corresponding to a narrow range of intensities of scattered light). This comparison is preferably carried out automatically by program software built in to the system so that the information may be fed back in real-time to effectuate selection of a subsequent sample or initiate a cleansing routine.

The flow cell system of the present invention saves light scatter data from samples in a unique way that enhances the data processing capabilities of the system. The total number of events for each of several different light scatter channel regions are collected and stored simultaneously. In a preferred embodiment, events for each of three different light scatter channel regions are collected and stored. These regions correspond to: an "All" channel range, corresponding to all, or substantially all of the channels available; an "M1" channel range corresponding to a similar channel grouping except that a number of channels at the low intensity end of the channel range are omitted; and an "M2" channel range that has yet a further deletions of a number of channels at the low intensity end of the channel range. For example, in one embodiment in a 256 channel detector system, the "all" channel range corresponds to channels 0-256; "M1" corresponds to channels 50–256; and "M2" corresponds to channels 90–256.

It is optimal to measure and accumulate the number of events at various intensities of light scattering simultaneously. As compounds precipitate the particle size changes and in a time-dependent manner. It is possible to detect these changes in one channel range, and yet find no difference if another channel range is chosen. The default method is to determine the light scattering data detected in the broadest channel range (Listed as "All"). Often, there is interference from the non-aqueous solvent used to prepare the dilutions of the test compound. For instance when compound samples are prepared from 10 mM solutions in DMSO, impurities may appear that cause the "All" range data unreliable, while the M1 or M2 each show a smooth curve when comparing the number of flashes in the channel range in relation to the concentration of compound tested.

The alignment data from beads may, however, be processed differently: Each time the alignment is checked, the bead position of the system is verified and if the preset bead criterion is met (number of beads counted within defined channel range) then the system saves the total number of beads counted. This information may be saved and printed with the sample results file when the sample grouping (such as for instance, the samples in a microtiter plate) is completed. Raw data files may be generated for both samples and alignment checks but only temporarily saved by the flow cell system until samples form the next microtiter plate are assayed.

In another alternative embodiment of the flow cell system, a dye is injected into the sample stream, the position of the sample stream may then be verified by image analysis from camera such as a CCD camera. The software of the flow cell system may be configured to detect changes in the sample stream. The system may then output this information, such as for example in alerting the operator of the system, or initiating one or more routines to correct the alignment automatically, preferably in real-time.

In yet another embodiment of the present invention the detection method depends on the refractive index difference between the sheath fluid and the sample stream. Refractive index differences may be used to track the sample liquid stream when the sheath fluid has a different refractive index from that of the sample liquid stream. The refractive index detection may be by any method, e.g. by the use of phase contrast detection. A limitation of this approach is that if the sheath and sample buffer have the same or very similar refractive indices then this method cannot be used.

EXAMPLE

Commercially available compounds from Sigma (pyrene, trifluralin and danazol) were obtained in powder form and subsequently dissolved in DMSO (concentration was adjusted to 25 mM). In 96 well micro plates, compound stocks were further diluted serially (1 to 2.5 fold) in DMSO to create a series of DMSO stocks for each compound (varying compound concentration). Finally, the diluted compound stocks for each compound were transferred in triplicate into second micro plate containing an aqueous buffer (pH 7.4, 1 to 100 dilution).

Light Scattering data was determined in a system according to the present invention by reading the plate approximately 30 minutes after mixing into the aqueous phase. Increasing light scatter events correlates with decreasing solubility. Compounds with lower solubility show significant light scatter events above background at low compound concentrations.

Figure 1C:
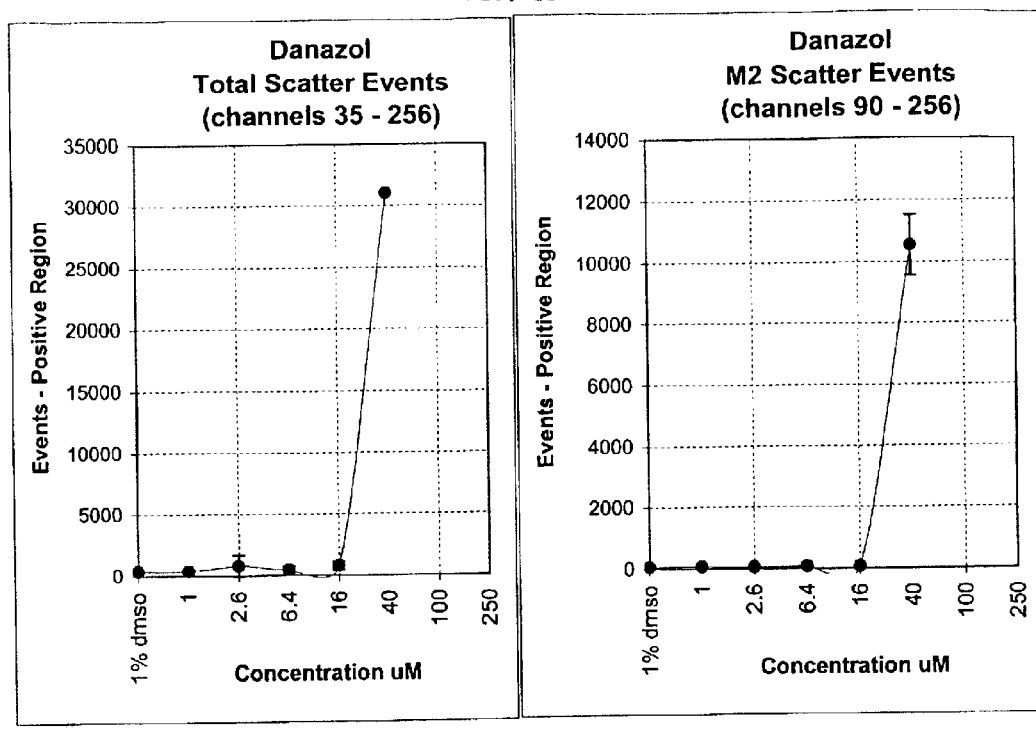

The results obtained, as shown in FIGS. 1A, 1B and 1C, according to the present invention, correlated well with the expected solubility of the three compounds. Light scatter events collected from an overlapping but more narrow channel range (M2 Scatter Events) confirmed the precipitation patterns observed in the original range. Channel ranges excluding smaller particles (such as the M2 range shown here) are often used to filter out (dim and variable) interfering scatter events (data not shown).

Analysis software may also be used to analyze the DMSO (or other non-aqueous solvent) and buffer only controls in relation to the compound samples. Different cutoff rules may be used to determine when the light scattered from a compound well is significantly above that scattered from the control well. Briefly, the total data from controls are compared to the total data from samples (and the same for the other regions). The cutoff significance rules are different for each of the regions because the higher number of events in the regions may include more light scattering events from solvent or contaminant particles. The latter may often be separated from events from precipitated particles of the test compound by size distribution. This occurs when there is a significant correlation between the number of events and the concentration of sample compound in one channel range, but not in another channel range. Software processing of the data may used according to this analysis to determine which of the channel ranges accurately and sensitively reflects the precipitation of the test compound from the saturated aqueous solution of the sample fluid.

The flow cell solubility testing system of the present invention is particularly well suited to high throughput solubility testing, as is needed for instance in the solubility testing of chemical libraries, such as combinatorial or other synthetic chemical compound libraries. The embodiments and examples provided herein are intended as illustrations and are not to be taken as limitations of the scope of the invention. Those of skill in the art will immediately recognize the full scope and applications of the present invention.

What is claimed is:

1. A flow cell system for solubility testing of a compound in a sample liquid, comprising:
   (a) a flow cell suitable for channeling a fluid sheath flowing through the flow cell, the fluid sheath directing a continuous or intermittent sample liquid stream, wherein the sample liquid stream comprises particles of the compound for solubility testing;
   (b) a light source for illuminating the sample liquid stream in the flow cell and producing scattered light flashes from the particles of the compound;
   (c) a detector for detecting the scattered light flashes and generating an electronic pulse detection signal for each light flash to provide raw sample data, each light flash having a light intensity and each electronic pulse detection signal having a pulse amplitude corresponding to the intensity of the detected light flash; and
   (d) a processor for real-time processing of multiple electronic pulse detection signals from said detector, wherein each of the signals is allocated to one of a series of channels, each channel detecting electronic pulse detection signals within a preset signal amplitude range, to provide multichannel sample data, and outputting the sample data for effectuating selection of a subsequent sample liquid from a plurality of subsequent sample liquids for solubility testing.

2. The flow cell system according to claim 1, further comprising a means for storage and recall of the raw sample data and/or the multichannel sample data.

3. The flow cell according to claim 1, wherein the subsequent sample liquids comprise one or more concentrations of the sample liquid.

4. The flow cell system according to claim 1, wherein the sample liquid and subsequent sample liquids are provided in wells of a microtiter plate.

5. The flow cell system according to claim 4, wherein the microtiter plate further comprises wells containing a control substance.

6. The flow cell system according to claim 1, further comprising a reservoir for containing a control substance, wherein the control substance is a particle or a bead.

7. The flow cell system according to claim 1, wherein the light source is a laser light source, a monochromatic light source or a halogen light source.

8. The flow cell system according to claim 1, wherein the scattered light is forward scattered, off angle scattered light or side scattered light.

9. The flow cell system according to claim 1, wherein the detector for detecting the scattered light flashes is a photomultiplier tube (PMT) detector or a semiconductor/diode detector.

10. A method for solubility testing of a compound in a sample liquid, comprising:
   (a) providing a flow cell suitable for channeling a fluid sheath flow through the flow cell, the fluid sheath flow directing a continuous or intermittent sample liquid stream, wherein the sample liquid stream comprises particles of the compound for solubility testing;
   (b) illuminating the sample liquid stream in the flow cell to provide scattered light flashes from the particles of the compound;
   (c) detecting the scattered light flashes to provide raw sample data and generating an electronic pulse detection signal for each light flash, each light flash having a light intensity and each electronic pulse detection signal having a pulse amplitude corresponding to the intensity of the detected light flash;
   (d) processing of multiple electronic pulse detection signals in real-time, wherein each of the signals is allocated to one of a series of channels, each channel detecting electronic pulse detection signals within a preset signal amplitude range; and
   (e) outputting the sample data to a means for effectuating a selection of a subsequent sample liquid from a plurality of subsequent sample liquids for solubility testing.

11. The method according to claim 10, further comprising storing the raw sample data and/or the multichannel sample data.

12. The method according to claim 10, wherein the sample liquid and subsequent sample liquids are provided in the wells of a microtiter plate.

13. The method according to claim 12, wherein the subsequent sample liquids comprise a series of higher concentrations of the compound for solubility testing and a series of increasing concentrations of a second compound for solubility testing; and wherein the method further comprises selecting one of the series of higher concentrations of the compound in the event that the multichannel sample data indicates the absence or low levels, of particles of the compound.

14. The method according to claim 12, wherein the subsequent sample liquids comprise a series of higher concentrations of the compound for solubility testing and a series of increasing concentrations of a second compound for solubility testing; and wherein the method further comprises: selecting one of the series of increasing concentrations of the second compound for solubility testing in the event that the multichannel sample data indicates the presence of significant levels of particles of the compound.

15. The method according to claim 12, wherein the microtiter plate comprises wells containing a control substance.

16. The method according to claim 15, wherein the control substance is a particle or a bead.

17. A method for solubility testing of a compound in a sample liquid, comprising:
   (a) providing a flow cell suitable for channeling a fluid sheath flow through the flow cell, the fluid sheath flow directing a continuous or intermittent sample liquid stream, wherein the sample liquid stream comprises particles of the compound for solubility testing;
   (b) illuminating the sample liquid stream in the flow cell to provide scattered light flashes from the particles of the compound;
   (c) detecting the scattered light flashes to provide raw sample data and generating an electronic pulse detection signal for each light flash, each light flash having a light intensity and each electronic pulse detection signal having a pulse amplitude corresponding to the intensity of the detected light flash;
   (d) processing of multiple said electronic pulse detection signals in real-time, wherein each of the signals is allocated to one of a series of channels, each channel detecting electronic pulse detection signals within a preset signal amplitude range; and
   (e) outputting the sample data to a means for effectuating a selection of a subsequent sample liquid from a plurality of subsequent sample liquids for solubility testing,
   wherein the sample liquid and subsequent sample liquids are provided in the wells of a microtiter plate and wherein the subsequent sample liquids comprise a series of higher concentrations of the compound for solubility testing and a series of increasing concentrations of a second compound for solubility testing; and wherein the method further comprises:
      (i) selecting one of the series of higher concentrations of the compound in the event that the multichannel sample data indicates the absence or low levels of particles of the compound; or
      (ii) selecting one of the series of increasing concentrations of the second compound for solubility testing in the event that the multichannel sample data indicates the presence of significant levels of particles of the compound.

18. A method for maintaining the sample stream alignment in a flow cell, comprising:
   (a) providing a flow cell suitable for channeling a fluid sheath flow through the flow cell, the fluid sheath flow directing a continuous or intermittent sample liquid stream, wherein the sample liquid stream comprises a control substance;
   (b) illuminating the sample liquid stream in the flow cell to provide scattered light flashes from the control substance;
   (c) detecting the scattered light flashes to provide raw control substance data and generating an electronic pulse detection signal for each light flash, each light flash having a light intensity and each electronic pulse detection signal having a pulse amplitude corresponding to the intensity of the detected light flash;
   (d) processing the multiple electronic pulse detection signals in real-time, wherein each of the signals is allocated to one of a series of channels, each channel detecting electronic pulse detection signals within a preset signal amplitude range to provide multichannel control substance data, and thereby determining whether the sample liquid stream is aligned or misaligned, and outputting an effectuator signal if the sample liquid stream is misaligned; and
   (e) initiating a corrective realignment process upon receiving the effectuator signal.

19. The method according to claim 18, wherein the control substance is a particle or a bead.

20. The method according to claim 18, wherein the control substance is introduced into the sample liquid stream intermittently.

21. The method according to claim 18, wherein the control substance is continuously present in the sample liquid stream.

22. The method according to claim 18, wherein the light source is a laser light source, a monochromatic light source or a halogen light source.

23. The method according to claim 18, wherein the detector for detecting light scattered by the control substance is a photomultiplier tube (PMT) detector or a diode detector.

24. The method according to claim 18, wherein the scattered light is forward scattered, off angle scattered light or side scattered light.

25. The method according to claim 18, wherein the detector also detects scattered light from compounds for solubility testing in the sample liquid stream.

26. The method according to claim 18, wherein the realignment process comprises introducing a cleansing agent into the sample liquid stream; backflushing the flow cell; or draining and refilling the flow cell.

27. The method according to claim 26, wherein the cleansing agent comprises an oxidizing agent or a bleach solution.

28. The method according to claim 18, further comprising selecting the control substance from a well of a microtiter plate or a control substance reservoir.

29. A processor for real-time processing of multiple electronic pulse detection signals from a flow cytometer adapted for solubility testing, wherein each of the signals is allocated to one of a series of channels, each channel detecting electronic pulse detection signals within a preset signal amplitude range, to provide multichannel sample data, and outputting the sample data for effectuating selection of a subsequent sample liquid from a plurality of subsequent sample liquids for solubility testing.

30. A processor for real-time processing of multiple electronic pulse detection signals from a flow cytometer adapted for solubility testing, wherein each of the signals is allocated to one of a series of channels, each channel detecting electronic pulse detection signals within a preset signal amplitude range to provide multichannel control substance data, and thereby determining whether the sample liquid stream is aligned or misaligned, and outputting an effectuator signal if the sample liquid stream is misaligned; and initiating a corrective realignment process upon receiving the effectuator signal.

31. A flow cell system for solubility testing of a compound in a sample liquid, comprising:
   (a) a flow cell suitable for channeling a fluid sheath flow through the flow cell, the fluid sheath flow directing a continuous or intermittent sample liquid stream, wherein the sample liquid stream comprises particles of the compound for solubility testing;
   (b) a light source for illuminating the sample liquid stream in the flow cell to provide scattered light flashes from the particles of the compound;
   (c) a detector for detecting the scattered light flashes to provide raw sample data and generating an electronic pulse detection signal for each light flash, each light flash having a light intensity and each electronic pulse detection signal having a pulse amplitude corresponding to the intensity of the detected light flash;
   (d) a processor for processing of multiple electronic pulse detection signals from the detector in real-time, wherein each of the signals is allocated to one of a series of channels, each channel detecting electronic pulse detection signals within a preset signal amplitude range; and
   (e) a selection device for receiving the sample data and for effectuating a selection of a subsequent sample liquid from a plurality of subsequent sample liquids for solubility testing,
   the selection device comprising a microtiter plate having wells for providing the sample liquid and subsequent sample liquids and wherein the subsequent sample liquids comprise a series of higher concentrations of the compound for solubility testing and a series of increasing concentrations of a second compound for solubility testing; and wherein the selection device comprises: (i) means for selecting one of the series of higher concentrations of the compound in the event that the multichannel sample data indicates the absence or low levels of particles of the compound; or (ii) means for selecting one of the series of increasing concentrations of the second compound for solubility testing in the event that the multichannel sample data indicates the presence of significant levels of particles of the compound.

* * * * *